United States Patent [19]
Heuft et al.

[11] Patent Number: 6,116,404
[45] Date of Patent: Sep. 12, 2000

[54] PROCESS AND DEVICE FOR CONVEYING CONTAINERS PAST A DEVICE FOR INSPECTING THE CONTAINER BASES

[75] Inventors: Bernhard Heuft, Burgbrohl; Hans-Ulrich Goller, Bonn-Bad Godesberg, both of Germany

[73] Assignee: Heuft Systemtechnik GmbH, BurgBrohl, Germany

[21] Appl. No.: 09/077,534

[22] PCT Filed: Nov. 25, 1996

[86] PCT No.: PCT/EP96/05192

§ 371 Date: May 28, 1998

§ 102(e) Date: May 28, 1998

[87] PCT Pub. No.: WO97/19766

PCT Pub. Date: Jun. 5, 1997

[30] Foreign Application Priority Data

Nov. 24, 1995 [DE] Germany ............... 295 18 639 U

[51] Int. Cl.[7] .................................................. B65G 47/00
[52] U.S. Cl. ...................... 198/339.1; 198/836.1
[58] Field of Search .............. 198/339.1, 836.1, 198/600, 462.1, 462.3, 443

[56] References Cited

U.S. PATENT DOCUMENTS

| | | | |
|---|---|---|---|
| 2,734,621 | 2/1956 | Mojonnier | 198/162 |
| 4,077,254 | 3/1978 | Mercer et al. | 73/94 |
| 4,158,624 | 6/1979 | Ford et al. | 198/367 |
| 4,915,237 | 4/1990 | Chang et al. | 209/524 |

FOREIGN PATENT DOCUMENTS

| | | |
|---|---|---|
| 0 124 164 A1 | 11/1984 | European Pat. Off. ....... G01N 21/90 |
| 0 415 154 B1 | 4/1995 | European Pat. Off. ......... B07C 5/34 |
| 2 314 794 | 11/1973 | Germany . |
| 28 10 941 | 10/1978 | Germany ....................... G01M 7/00 |
| 27 17 955 | 3/1979 | Germany ........................ B67C 1/14 |
| 29 04 126 | 8/1980 | Germany ........................ B08B 9/46 |
| 41 30 155 A1 | 3/1993 | Germany ........................ B08B 9/42 |
| 93 10 623 U | 12/1993 | Germany ........................ B07C 5/36 |
| 42 37 234 C1 | 4/1994 | Germany ....................... B65G 17/00 |
| 43 30 796 A1 | 3/1995 | Germany ....................... B65G 47/68 |
| 785223 | 11/1995 | United Kingdom . |

OTHER PUBLICATIONS

"Pet Hanlding" Ling Systems Limited; St. Neots, Huntingdon, Cambs PE19 3JH; England; Nov. 1993.

Primary Examiner—Christopher P. Ellis
Assistant Examiner—Khoi H. Tran
Attorney, Agent, or Firm—Gardner, Carton & Douglas

[57] ABSTRACT

Containers are conveyed past an apparatus for inspecting the bottom of the containers for contamination, flaws and foreign bodies. To that end, the containers are fed into the inspection apparatus by a first conveyor, and guided out of the inspection apparatus on a second conveyor, in which a gap is left between the first and second conveyors, within which the containers are not supported, at least not over the whole of their under surface. The containers on the first conveyor, within the gap and on the second conveyor are guided by side guidance apparatus and are conveyed under dynamic pressure, at least within the gap.

19 Claims, 5 Drawing Sheets

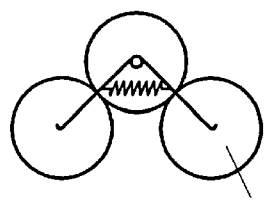
Fig. 8
35
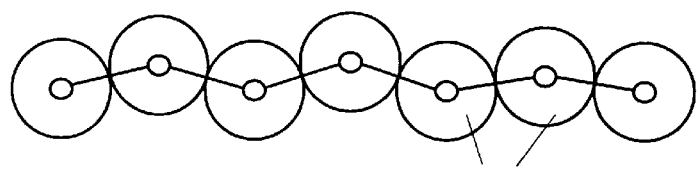
35   Fig. 9
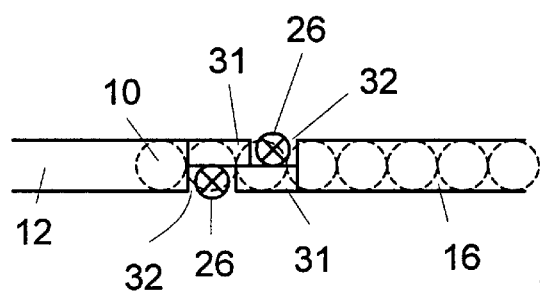
Fig. 6
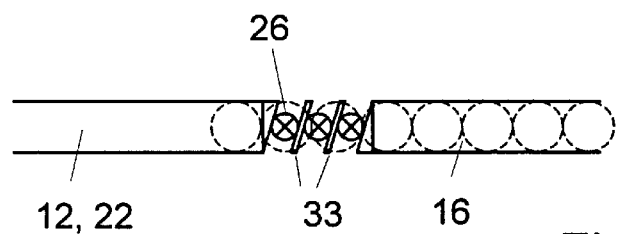
Fig. 7

PROCESS AND DEVICE FOR CONVEYING CONTAINERS PAST A DEVICE FOR INSPECTING THE CONTAINER BASES

BACKGROUND OF THE INVENTION

The invention relates to a method and a device for conveying containers past an apparatus for inspecting the bottom of the containers, for example for contamination, flaws and foreign bodies. The containers are guided into the inspection apparatus on a first conveyor, and guided out of the inspection apparatus on a second conveyor. A gap is left between the first and second conveyors, within which the containers are inspected by the inspection apparatus and within which the containers are not supported, at least not over the whole of their under surface. The containers are guided by side guidance apparatus.

Conveyor devices of this type are employed particularly for the inspection of empty bottles (empty glass or plastic bottles). In this case, the inspection apparatus consists of a light source arranged in the region of the gap below the empty bottles, and of a recognition device, for example a CCD camera, arranged above the empty bottles, this device inspecting the bottom of the empty bottles through the mouth of the bottle.

It is known from EP-A-0 124 164 and EP-B1-0 415 154 to hold the empty bottles by their sides between belts moving along with them, and thus to move them forwards over the gap.

It is also known to grip empty bottles in star-shaped wheels, and thus to guide them through an apparatus for inspecting the bottom.

In both instances the containers, for example empty bottles, have first of all to be lined up singly, so that they can be delivered in a row on the first conveyor with a fixed minimum spacing from each other, or at least without pressure being applied (without dynamic pressure). The containers are lined up singly by means of special-purpose apparatus. After the inspection, the containers are again fed along under dynamic pressure, because the typical filling machinery requires the containers at the entry to the filling machine to be moved under dynamic pressure. When being moved by dynamic pressure, the containers, which are not in any order, are moved forwards on a conveyor belt or on a stationary surface under pressure from the containers following behind. In this case, there is a rail beside the conveyor belt or the stationary surface, to prevent the containers falling over.

SUMMARY OF THE INVENTION

The object of the invention is to simplify the conveying of containers in the region of inspection apparatus, during which the containers are moved over a gap between two conveyors.

This object is achieved with a method and a device of the type mentioned at the outset, by conveying the containers under dynamic pressure, and by the fact that the side guidance apparatus, which is located on both sides of the first and second conveyors and in the region of the gap between the conveyors, is so designed that the containers can be conveyed under dynamic pressure.

In order for the containers to be conveyed under dynamic pressure, they mutually support each other. The mutual pressure is sufficient to hold the containers within a gap which can amount to 3 times the diameter of the containers, and so to bridge this gap without a "solid floor". The friction between the containers pressing against each other is thus sufficient to prevent the containers sliding vertically with respect to each other. The containers themselves can particularly be jars or glass or plastic bottles. The containers may be rotationally symmetric or have an angular cross-section.

Special provisions can be made with regard to the start of operations and the end of operations, since at the start of operations no back pressure is yet available, and at the end of operations no further pressure is generated from bottles following behind. Several possibilities exist in this respect:

Firstly, a fixed, narrow, neck guide can be provided, in the form of low-friction, fixed rails, which catch crown cork bottles under the mouth bead, catch screw-top bottles under the threaded top, and catch other containers at similarly formed places, so that, at the start of operations, the containers are pushed over the gap between the conveyors by the containers following behind without them being able to slip through and fall out.

Secondly, a protective glass plate, which is fitted above the light source of the inspection apparatus arranged under the gap, can be raised temporarily to the level of the conveyors at the start of operations, so that the containers can slide smoothly from the first conveyor to the second conveyor. When the required dynamic pressure is established, and when the containers are thereby self-supporting above the gap, the protective glass plate is lowered by a few millimeters within the gap, so that no direct contact remains between the containers and the protective glass plate, and wear is thereby prevented.

It is important that both the neck guide and the protective glass plate are configured in such a way that they are not loaded by the containers in normal operation, that is to say when the containers are conveyed under dynamic pressure and when they are supporting each other in the bottom-inspection region and are supported by the side guidance apparatus. For that reason, the neck guide is arranged to be slightly lower than the position in which the mouth bead and the threaded top of the crown cork and screw-top bottles respectively are located. That being so, the neck guide in normal operation catches the necks of the bottles only on the side, and so does not carry the weight of the bottles. Only when, at the start of operations, the end of operations or during interruptions in operations, the bottles are not under dynamic pressure, and, for that reason, the bottles are not supported by the adjacent bottles and the side guidance for bottom inspection in the gap between the two conveyors, and when consequently they sink downwards, are they supported by the neck guide. In the same way, the protective glass plate is arranged slightly under the level of the conveyors, so that the bottles contact the protective glass plate, and are supported by it, only when the dynamic pressure is absent.

As for the side guidance apparatus in the gap region, this can be a continuation of the side rails, which are required for conveying under dynamic pressure along the first and second conveyor. A third possibility for remedying the problems arising at the beginning of operations consists in interrupting one or both side rails within the gap and in substituting instead a foam or rubber roller with a vertical axis of rotation. These rollers are arranged at a distance from the rail or from the roller located opposite, this distance being less than the diameter of the containers. In order for the containers to be held singly by the inspection device, the width of the first conveyor, that is to say the spacing between the side rails of the first conveyor, should not be greater than about 1.2 times the diameter of the containers, and advantageously only a few millimeters more than the diameter of the containers. The rollers can be free-running or driven. The rollers hold the containers only within the gap between the conveyors and only in this region is the side rail replaced by the rollers.

A fourth possibility consists in generating the required dynamic pressure by conveying special ancillary apparatus at the start of operations. This ancillary apparatus may consist of one or more mechanically coupled cylindrical bodies, which are placed by hand on the first conveyor. When the ancillary apparatus consist of a single body, the body normally has a diameter or a diagonal which is greater than the spacing between the side rails of the conveyor, and the body can be distorted, given that it consists, for example, of elastic material, or its side walls lying against the rail are under spring pressure. Due to the friction arising between the body and the rail, such an ancillary apparatus sets up a resistance to the pressure applied by the following containers which simulates the dynamic pressure. With three or more bodies, these will be arranged into a triangular or zigzag shape mechanically under spring pressure, so that they press against the opposite rails of the conveyor and thereby offer resistance to the movement of the containers. The ancillary apparatus can also be so designed that a braking force is exerted on the axes of the bodies, which opposes the rotation of the bodies. The containers following immediately behind an ancillary apparatus of this type therefore behave in the same way as when being conveyed under dynamic pressure. Likewise, at the end of operations, an ancillary apparatus in the shape of a multi-part body can be placed after the last container on the first conveyor, so that the multi-part body, by virtue of the coupling of its individual elements, generates the required pressure and, because of its length, can bridge the gap. The overall length of the ancillary apparatus in this case is advantageously at least twice the length of the gap, so that the ancillary apparatus can bridge the gap without difficulty. The ancillary apparatus can subsequently be removed automatically from the stream of containers by a lead-out device. It is also possible to position it, by means of an automatic recovery apparatus, ready for the next use at the entry to the installation, and then to feed it in again automatically.

The possibility also exists of dividing the bottom inspection into two or more parts, so that within the route of the conveyor there is never a gap which is larger than the diameter of a container, or so that it is always guaranteed that one side of the containers is still guided on a firm base. The gap between the two conveyors can be bridged by a metal plate, for example, which reveals mutually offset empty spaces. The left-hand half of the metal plate can be left open first, over a length corresponding to the container diameter, and then the right-hand half, so that the left-hand side of the container bottom is inspected first, and then the right-hand side. It is also possible, between the two conveyors, to provide guides or metal plates running obliquely or crosswise at the conveyor level, over which the containers are pushed while they are being inspected. The recognition apparatus used for the inspection can in this case consist of several cameras for the individual inspection regions, or of a single camera with optical picture splitting, which may be carried out by mirrors.

Combinations of these possibilities can be envisaged, particularly in that the ancillary facilities presented as the fourth possibility can be used in combination with one of the other devices, since these ancillary devices are the only possibility for working under dynamic pressure up to the end of operations.

The method and device in accordance with the invention are particularly suitable for inspecting empty bottles at low and medium capacity, that is to say with a throughput of up to 36,000 bottles/hour although higher speeds are certainly also possible.

Exemplary embodiments of the invention will be explained below by means of the figures. These show:

BRIEF DESCRIPTION OF THE DRAWINGS

FIG. 6 a conveyor device, in which the containers are supported on only a part of their under surface between the conveyors, in plan view;

FIG. 7 an exemplary embodiment similar to that of FIG. 6, in which the containers are supported by strips arranged obliquely in the gap region between the conveyors;

FIGS. 8 and 9 ancillary apparatus for achieving a dynamic pressure at the start and end of operations;

DETAILED DESCRIPTION OF THE INVENTION

Figure 1:
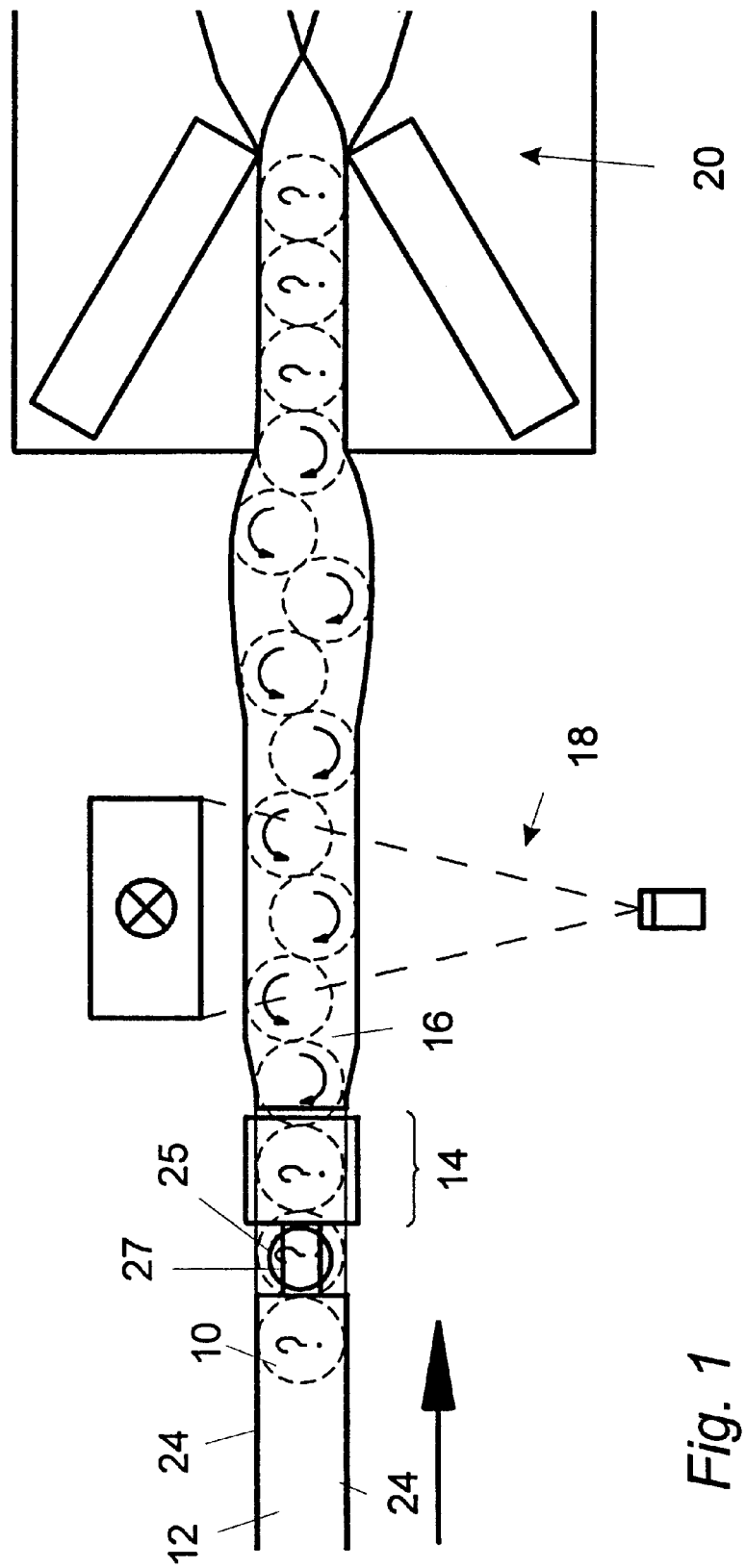
FIGS. 1 and 2 an installation for inspecting empty bottles, in plan and side view respectively.
Figure 2:
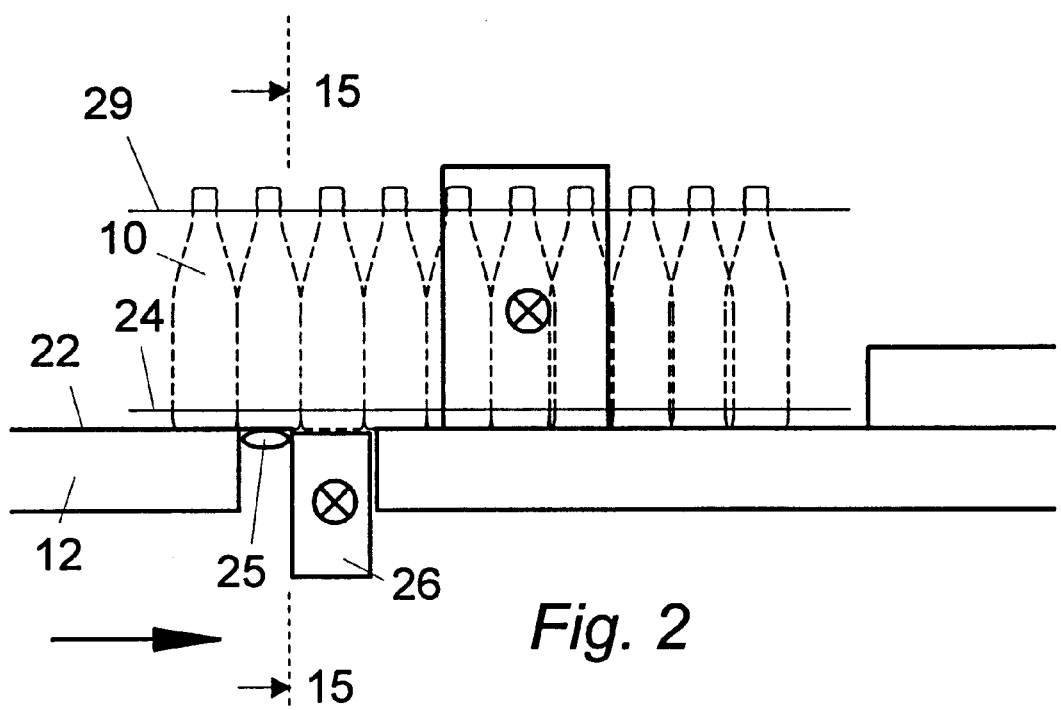

FIGS. 1 and 2 show an installation for inspecting empty bottles. The empty bottles 10 are led in on a first conveyor 12, undergo a bottom inspection within a gap 14, then are moved along on a second conveyor 16 and led past a side wall inspection station 18 to an outlet station 20. The first and second conveyors 12, 16 can be conventional conveyor belts or chain link conveyors. They are of well-known construction and will therefore not be described further here. The conveyors 12, 16 can also be of another construction, and the containers can be supported by air cushions, cylinders etc. As for the conveyors 12, 16, these may even be stationary plates, over which the containers are pushed by an apparatus generating dynamic pressure, for example a star-shaped wheel or a chain link conveyor. The conveyors 12, 16 define a conveyor level 22, at which the empty bottles 10 stand. To the side, at a short distance above the conveyor level 22, there are rails 24 provided on both sides as devices for guiding the empty bottles 10. By means of the rails 24, the bottles, which are under dynamic pressure, are held on the first and second conveyors 12, 16. To that end, the rails are of very stable construction. The rail 24 is extended from the first conveyor 12 over the gap 14 to the second conveyor 16.

Figure 15:
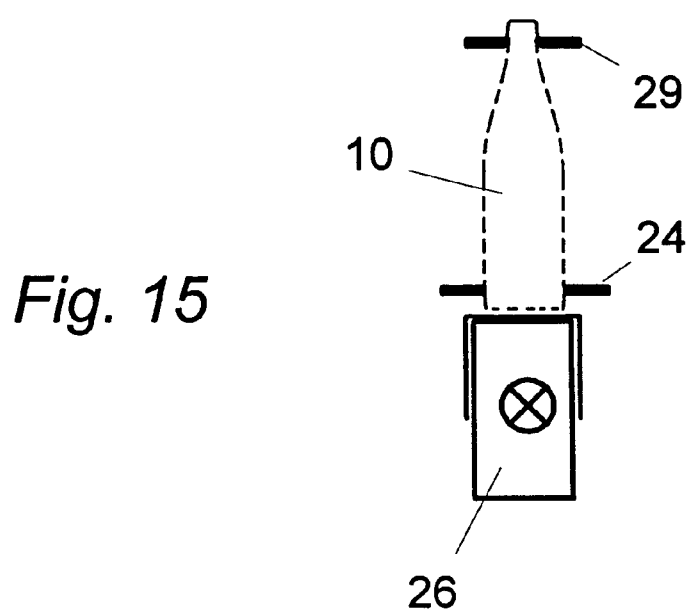
FIG. 15 a section through 15—15 of FIG. 2.

Within the gap 14 the empty bottles 10 are not supported from below. They hold each other by virtue of the pressure exerted on each other and by virtue of the friction with the rail 24. The width of the first and second conveyors 12, 16, that is to say the distance separating the two rails 24, is only slightly greater than the diameter of the empty bottles 10. In this way a gap 14 can be bridged, amounting in length to up to 3 times the diameter of the empty bottles 10. At the end of the first conveyor 12 a bottom blower 25 is set up, which blows clean the bottom of the empty bottles from beneath by means of a blast of air, so that drops of water or clinging particles are blown off the bottom. The bottom blower 25 is an air nozzle protruding from the middle of a mushroom-shaped head. The empty bottles are led by guides 27 over the bottom blower, so that the empty bottles 10 are still supported at the bottom blower 25. In order to allow the empty bottles to be moved over the gap 14, both at the start and at the end of operations when no dynamic pressure has yet been developed or when there are no more bottles following behind to exert dynamic pressure respectively, a neck guide 29 (FIG. 15) is provided in the gap 14 region; this guide catches the empty bottles by the neck directly below the mouth bead or the threaded top, and in that way prevents the bottles 10 dropping into the gap 14 in the absence of dynamic pressure. The neck guide 29 is set slightly lower, so that in normal operation, when the empty bottles are under dynamic pressure, a slight separation exists between neck guide and mouth bead or threaded top respectively. The neck guide 29 then does actually guide the neck of the bottle from the side, but does not bear the weight of the empty bottles, so that wear is reduced as much as possible.

Within the gap 14, under the conveyor level 22, there is a light source 26 which illuminates the empty bottles 10 from beneath. A recognition apparatus with a CCD camera is located above the empty bottles 10. The apparatus for inspecting the bottom of the empty bottles 10 is of conventional construction and will therefore not be described further.

Figure 3:
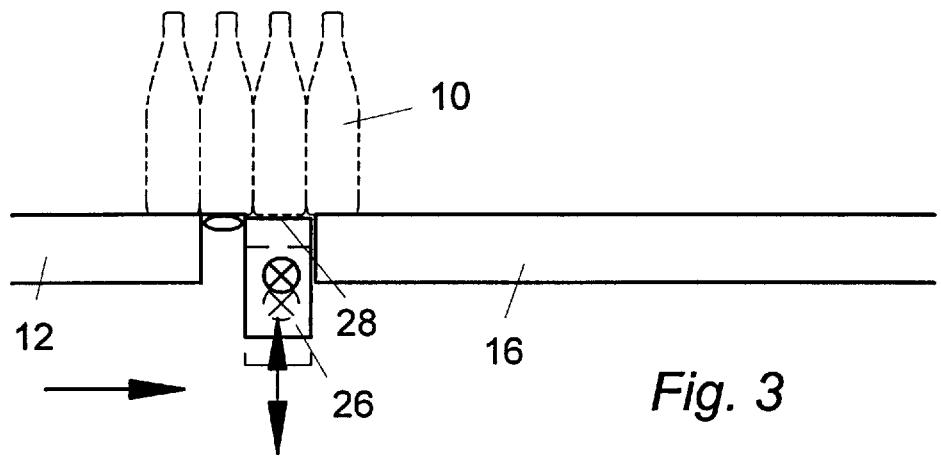
FIG. 3 a conveyor device with a protective glass plate which can be raised into the gap region.

In the embodiment shown in FIG. 3, the light source 26 is installed so as to be movable in the vertical, and has its upper surface covered over by a protective glass plate 28. That being so, the possibility exists, at the start of operations, when the empty bottles 10 are not yet under dynamic pressure, of raising the light source up higher, so that the gap 14 between the first and second conveyor 12, 16 is bridged by the protective glass plate 28 of the light source 26. As soon as the dynamic pressure has been established within the row of empty bottles 10, the light source 26 can be moved downwards, because the empty bottles 10 within the gap 14 no longer require any additional support.

Figure 4:
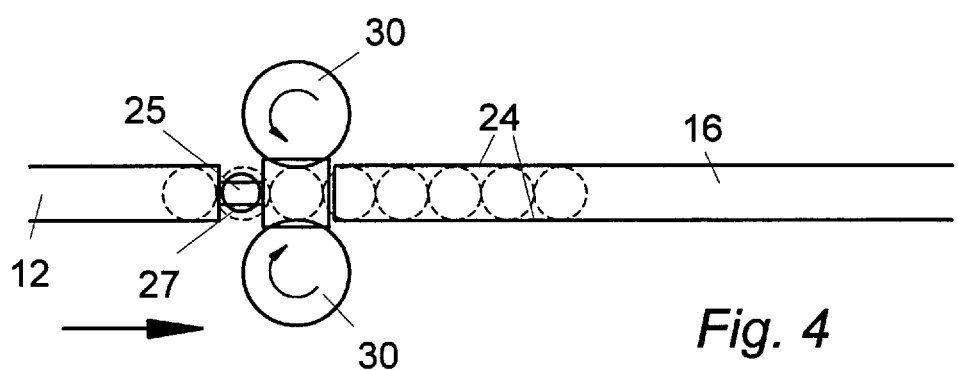
FIGS. 4 and 5 a conveyor device with sponge or rubber rollers arranged at the side of the gap region, in plan and side view respectively.
Figure 5:
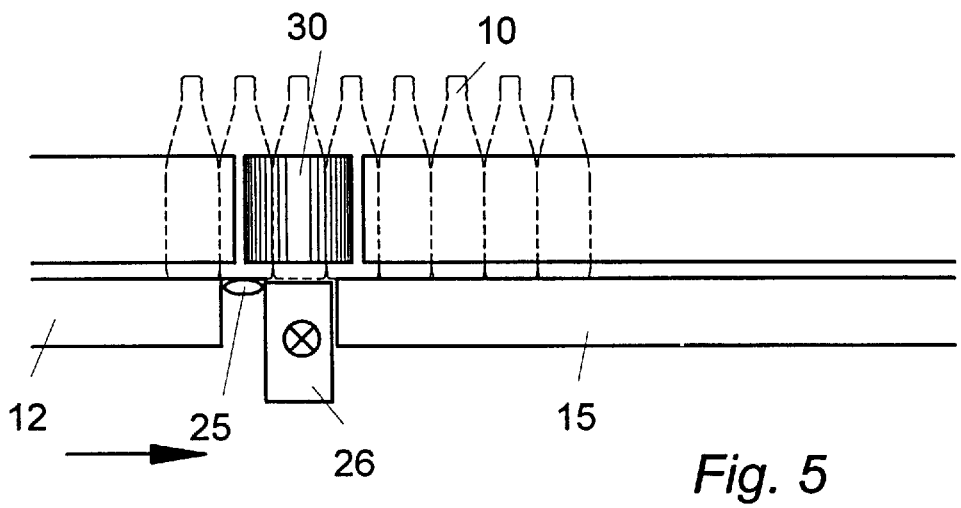

Another possibility for overcoming the difficulties arising at the start of operations consists in substituting the rails 24 in the gap 14 region by sponge or rubber rollers 30, which are arranged sufficiently close to the gap 14, with their axis of rotation vertical, that they bear against the sides of the empty bottles 10 (FIGS. 4 and 5). In that way, the empty bottles 10 are prevented from dropping into the gap 14 when no dynamic pressure is present. To that end, the spacing between the two sponge or rubber rollers 30 is less than the diameter of the empty bottles 10.

A further possibility for avoiding difficulties at the start of operations consists, in accordance with FIG. 6, in providing support plates 31 within the gap, the width of these plates corresponding to about half the distance separating the rails 24 (not included in FIG. 6), so that two regions 32 exist, offset from each other, between the first and second conveyors 12, 16, within which regions 32 the empty bottles 10 are not supported. The width of these regions corresponds to about half the diameter of the empty bottles, and the length of these regions 32 is somewhat greater than the diameter of the empty bottles. The two regions 32 are offset from each other in the conveying direction so that they do not overlap each other. In this way, the empty bottles 10 are still able to be guided by one side on the support plates 31.

In a similar way, in accordance with FIG. 7, guides 33 can be arranged running obliquely within the gap 14 at the conveyor level 22, such that the distance separating the guides 33 in the conveying direction corresponds to about half the diameter of the empty bottles 10. The guides 33 can also run at right angles to the conveying direction. The inspection of the bottom of the empty bottles 10 takes place within the space between the guides 33. To that end, the recognition apparatus may consist of several cameras for the individual spaces. It may also consist of a single camera with corresponding optical picture splitters, which are formed by mirrors. In FIG. 7, the rail 24 is likewise not depicted, for reasons of clarity.

Difficulties also arise at the end of operations, in that the last empty bottles 10 are not fed in under dynamic pressure, and that, under certain circumstances, the impetus of their movement may not be sufficient to move them over the gap 14 without power being applied. The difficulties arising both at the start and at the end of operations due to the lack of dynamic pressure can be overcome by having two, or better three or more, cylindrical bodies 35 mechanically coupled in the way shown in FIGS. 8 and 9, and having these coupled bodies 35 run through in front of the empty bottles at the beginning of operations, and after the last empty bottles at the end of operations. In accordance with FIG. 8, three bodies 35 are flexibly linked together, in a triangular configuration, by means of a spring which pulls the two end bodies 35 towards each other. The diameter of the bodies 35 corresponds approximately to that of the empty bottles 10, and with the triangular configuration of the bodies 35 shown in FIG. 8, the two end bodies 35 and the middle body 35 each press against the rails 24 lying opposite and unbend on them.

Another possibility consists in linking a larger number of bodies 35 in a straight line or in a zigzag line, as shown in FIG. 9. So that the bodies 35 can exert a sufficient pressure on the preceding empty bottles 10, the bodies 35 are suitably heavier than the empty bottles 10 and/or their under surface is provided with a higher-friction coating than the under surfaces of the empty bottles 10 have.

Figure 10:
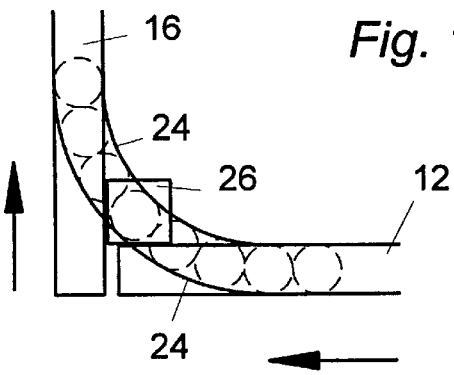
FIGS. 10 to 14 exemplary embodiments for the configuration of the conveyors.
Figure 11:
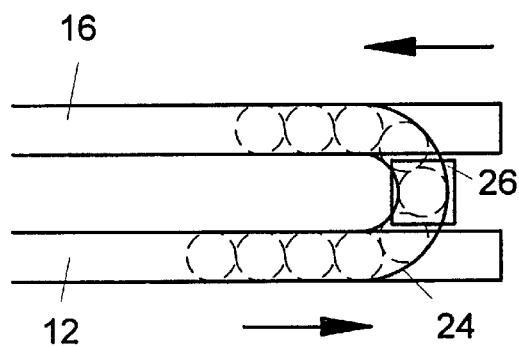
Figure 12:
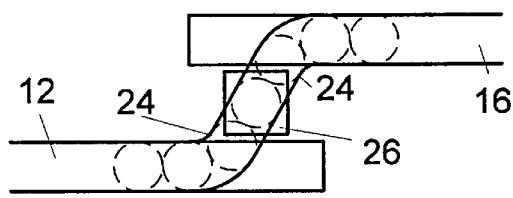

In the exemplary embodiments described above, the first and second conveyors 12, 16 were aligned with each other in a straight line. The two conveyors 12, 16 can, however, also be arranged at right angles to each other, such that the empty bottles 10 are guided along a curved path 36 (FIG. 10) from the first conveyor 12 to the second conveyor 16, and such that, in the angle between the two conveyors 12, 16, they are held only by the rail 24 and the pressure existing between the empty bottles 10 without any support from below. In accordance with FIG. 11, the two conveyors 12, 16 can also be arranged parallel to and separated from each other, or, in FIG. 12, offset and parallel to each other, such that the gap 14 is formed from the distance separating the conveyors 12, 16.

Figure 13:
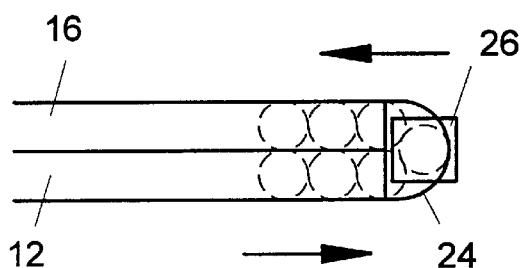

In accordance with FIG. 13, the two conveyors 12, 16 can also be arranged parallel to each other with no separation, and the gap 14, with the bottom inspection located within it, lies in a semi-circular region, in which the empty bottles 10 are transferred from the end of the first conveyor 12 onto the second conveyor 16.

Figure 14:
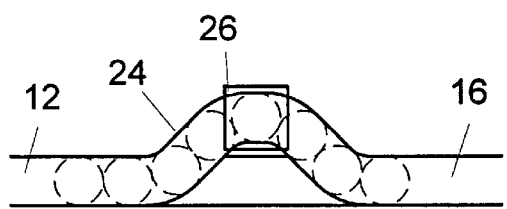

In accordance with FIG. 14, the first and second conveyors 12, 16 can also be formed by a single conveyor belt, in which the two rails 24 form a bulge, within which the empty bottles 10 are guided over a short section, without any support, adjacent to the conveyor belt, so that this short section constitutes the gap 14.

With regard to the side wall inspection station 18 and the lead-out station 20, reference will be made to the simultaneously filed PCT application "method and device for turning rotationally symmetric containers, such as bottles, while being conveyed under dynamic pressure" (our reference number 30560/autorotation), and the likewise simultaneously filed PCT application "device for leading out one or more rotationally symmetric containers from a stream of rotationally symmetric containers delivered under dynamic pressure, and cylinder with controlled extensible piston" (our reference number: 30561/grab)

What is claimed is:

1. A method for conveying a plurality of containers past an inspection apparatus for inspecting a bottom side of a plurality of containers comprising the steps of:

feeding the container into the inspection apparatus by means of a first conveyor;

guiding the container out of the inspection apparatus on a second conveyor;

leaving a gap between the first and second conveyors within which the containers are at least partly unsupported and within which the containers are inspected;

guiding the containers on the first conveyor, within the gap, and on the second conveyor by a side guidance apparatus;

conveying the containers at least within the gap under dynamic pressure; and wherein the dynamic pressure is a mutual pressure of the containers sufficient to hold the containers within the gap between the first and second conveyors so that the friction between the containers pressing against each other prevents the containers from sliding vertically with respect to each other.

2. The method according to claim 1 wherein the containers are not supported on their bottom side within the gap.

3. The method according to claim 1 further comprising the step of increasing the dynamic pressure during conveyance by feeding a plurality of coupled cylindrical bodies into the inspection apparatus before or after containers are fed into the inspection apparatus.

4. A device conveying a plurality of containers past an inspection apparatus for inspecting a bottom of the containers comprising:

a first conveyor for guiding a plurality of containers having a bottom surface into an inspection apparatus;

a second conveyor for guiding a plurality of containers from the inspection apparatus; wherein a gap is left between the first and second conveyor within which the containers are at least partly unsupported on the bottom surface and in which the inspection apparatus inspects the containers within the gap;

at least one side guidance apparatus extending on both sides of the first and second conveyors and the gap, wherein the side guidance apparatus permits the containers to be conveyed under dynamic pressure; and wherein the dynamic pressure is a mutual pressure of the containers sufficient to hold the containers within the gap between the first and second conveyors so that the friction between the containers pressing against each other prevents the containers from sliding vertically with respect to each other.

5. The device according to claim 4 wherein the containers are not supported on their bottom side within the gap.

6. The device according to claim 5 wherein the side guidance apparatus includes stationary rails.

7. The device according to claim 6 further comprising a transparent plate arranged within the gap, wherein the transparent plate can move upwards to the level of the conveyors to support the containers, and is lowered while the containers are being conveyed under dynamic pressure.

8. The device according to claim 4 further comprising a plurality of coupled cylindrical bodies, wherein dynamic pressure is increased during conveyance by feeding said plurality of coupled cylindrical bodies into the inspection apparatus before or after the containers are fed into the inspection apparatus.

9. The device according to claim 4 wherein the side guidance apparatus includes stationary rails.

10. The device according to claim 4 wherein the containers are bottles with a thickening at a top end of a neck, further comprising:

a static neck guide arranged below the thickening of the bottles so that a slight separation exists between the neck guide and the thickening at the top end of the neck when the dynamic pressure has been developed.

11. The device according to claim 4 further comprising a transparent plate arranged within the gap, wherein the transparent plate can move upwards to the level of the conveyors to support the containers, and is lowered while the containers are being conveyed under dynamic pressure.

12. The device according to claim 11 wherein the side guidance apparatus includes stationary rails.

13. The device according to claim 11 wherein the containers are not supported on their bottom side within the gap.

14. The device according to claim 4, further comprising a glass plate arranged within the gap, slightly below the level of the first and second conveyors.

15. The device according to claim 4 wherein the side guidance apparatus is formed within the gap by elastic rollers with vertical axes of rotation, where the distance separating the surfaces of the rollers is slightly less than the diameter of the containers, having a contact region having a length equal to or less than the length of the gap.

16. The device according to claim 15, wherein the containers are not supported on their bottom side within the gap.

17. The device according to claim 15 wherein the side guidance apparatus includes stationary rails.

18. The device according to claim 4 further comprising support plates arranged within the gap to reveal spaces which each extend from first and second conveyors to the middle of the gap wherein the support plates have a length in the conveying direction of approximately the diameter of the containers.

19. The device according to claim 4, wherein guides are arranged at least partly crosswise within the gap such that the distance separating the guides corresponds to approximately half the diameter of the containers.

* * * * *